(12) United States Patent
Xu et al.

(10) Patent No.: US 12,343,005 B2
(45) Date of Patent: Jul. 1, 2025

(54) MINIMALLY INVASIVE KNOTTER

(71) Applicant: NANJING DRUM TOWER HOSPITAL, Jiangsu (CN)

(72) Inventors: Can Xu, Jiangsu (CN); Dongjin Wang, Jiangsu (CN)

(73) Assignee: NANJING DRUM TOWER HOSPITAL, Nanjing (CN)

( * ) Notice: Subject to any disclaimer, the term of this patent is extended or adjusted under 35 U.S.C. 154(b) by 0 days.

(21) Appl. No.: 18/855,495

(22) PCT Filed: Mar. 5, 2024

(86) PCT No.: PCT/CN2024/080031
§ 371 (c)(1),
(2) Date: Oct. 9, 2024

(87) PCT Pub. No.: WO2025/107444
PCT Pub. Date: May 30, 2025

(65) Prior Publication Data
US 2025/0160821 A1 May 22, 2025

(30) Foreign Application Priority Data
Nov. 21, 2023 (CN) .......................... 202311552127.X

(51) Int. Cl.
*A61B 17/04* (2006.01)
(52) U.S. Cl.
CPC .............................. *A61B 17/0482* (2013.01)

(58) Field of Classification Search
CPC ............ A61B 17/0482; A61B 17/0487; A61B 17/0483; A61B 17/0485; A61B 17/0488;
(Continued)

(56) References Cited

U.S. PATENT DOCUMENTS 4,445,513 A * 5/1984 Ulrich ................ A61B 17/7008
606/256
5,026,376 A * 6/1991 Greenberg ......... A61B 17/1739
606/104
(Continued)

FOREIGN PATENT DOCUMENTS

| CN | 101801278 A | 8/2010 |
| CN | 102470004 A | 5/2012 |

(Continued)

*Primary Examiner* — Dianne Dornbusch
(74) *Attorney, Agent, or Firm* — Muncy, Geissler, Olds & Lowe, P.C.

(57) ABSTRACT

A minimally invasive knotter includes a first forcep handle, a second forcep handle, and a clamping head; middle parts of the first forcep handle and the second forcep handle intersect and are connected in a hinged manner, the first forcep handle includes an installation head, and a rotating rod is spherically hinged to the installation head; the clamping head is connected to the rotating rod; the second forcep handle includes a limiting clamp and a moving component; one side of the limiting clamp includes an opening; the limiting clamp is connected to the second forcep handle through the moving component so as to limit the clamping head at a set angle; an end part, backing away from the rotating rod, of the clamping head includes two clamping rods; and the two clamping rods approach to or move away from each other by a power component.

10 Claims, 8 Drawing Sheets

(58) Field of Classification Search
CPC ............ A61B 17/2812; A61B 17/2816; A61B 17/282; A61B 17/2825; A61B 17/2829; A61B 17/29; A61B 2017/0488; A61B 2017/049; A61B 2017/2926; A61B 2017/2929
See application file for complete search history.

(56) References Cited

U.S. PATENT DOCUMENTS

| | | | | |
|---|---|---|---|---|
| 5,735,857 | A * | 4/1998 | Lane | A61F 2/4607 81/418 |
| 9,550,277 | B1 * | 1/2017 | Williams | A61B 17/8866 |
| 2014/0277109 | A1 | 9/2014 | Alshomer et al. | |
| 2023/0030563 | A1 | 2/2023 | Sauer | |

FOREIGN PATENT DOCUMENTS

| | | | |
|---|---|---|---|
| CN | 105611864 | A | 5/2016 |
| CN | 108618817 | A | 10/2018 |
| CN | 111281454 | A | 6/2020 |
| CN | 111789662 | A | 10/2020 |
| CN | 216167617 | U | 4/2022 |
| CN | 115054299 | A | 9/2022 |
| CN | 115068065 | A | 9/2022 |
| CN | 115919386 | A | 4/2023 |
| CN | 117322934 | A | 1/2024 |

\* cited by examiner

MINIMALLY INVASIVE KNOTTER

TECHNICAL FIELD

The present disclosure belongs to the technical field of medical knotters, and particularly relates to a minimally invasive knotter.

BACKGROUND

The minimally invasive knotter is a medical device used for ligating and suturing in minimally invasive surgery. It usually consists of a handle and a head provided with a well-designed ligating hook or suturing needle. The minimally invasive knotter can be inserted into the body through a small incision, used for ligating blood vessels, suturing tissues, or repairing wounds. This instrument is more precise and operates faster in the surgical process, and can reduce postoperative pain and shorten postoperative recovery time. The minimally invasive knotter has been widely used in lots of surgery, including thoracoscopy surgery, laparoscopy surgery, arthroscopy surgery and the like.

A Chinese patent discloses a minimally invasive surgical knotter (authorized publication patent number of CN216167617U). The patented technology involves two forcep handles and a pin shaft. Middle parts of the two forcep handles are connected by the pin shaft to form a scissor fork body. The scissor fork body is provided with an adjusting part and a clamping part, and one end of the forcep handle is provided with a ring. According to the patented technology, fixing can be achieved by clamping an arc-shaped clamping block in an arc-shaped clamping groove so as to adjust the opening size of the clamping part in the scissor fork body, and the arc-shaped clamping block can be manually moved and clamped in the arc-shaped clamping groove.

However, in practical use of this patented technology, when it is necessary to suture the patient's wound, an operator needs to hold the ring for a long time, which can easily cause fatigue and increase the operation difficulty of the operator. At the same time, if the operator accidentally shaking hands due to fatigue, it can also aggravate the patient's wound.

Therefore, those skilled in the art have proposed a minimally invasive knotter.

SUMMARY

The present disclosure aims to overcome the defects in the prior art and provides a minimally invasive knotter, which has the advantages of being labor-saving and facilitating use when held by an operator.

The present disclosure provides the following technical solution:

provided is a minimally invasive knotter, including a first forcep handle, a second forcep handle, and a clamping head, where middle parts of the first forcep handle and the second forcep handle intersect and are connected in a hinged manner, the first forcep handle is provided with an installation head, and a rotating rod is spherically hinged to the installation head; the clamping head is connected to the rotating rod;

the second forcep handle is provided with a limiting clamp and a moving component; one side of the limiting clamp is provided with an opening capable of catching the clamping head; the limiting clamp is connected to the second forcep handle through the moving component so as to limit the clamping head to work at a set angle; and an end part, backing away from the rotating rod, of the clamping head is provided with two clamping rods, and under the action of a power component, the two clamping rods can approach to or back away from each other to achieve clamping and releasing of a suture line.

Preferably, the moving component includes a threaded rod, an adjusting nut, and a flat key; the second forcep handle is provided with an accommodating channel inwardly recessed from an end face; one end of the threaded rod extends into the accommodating channel, and the other end is connected to the limiting clamp; the end, extending into the accommodating channel, of the threaded rod is provided with a keyway extending in an axial direction of the threaded rod; the flat key is installed on a channel wall of the accommodating channel and is slidably connected to the keyway; an end face of the adjusting nut is provided with a connecting cylinder extending in an axial direction thereof; the connecting cylinder is rotatably connected to the second forcep handle; and a threaded hole of the adjusting nut is connected to the threaded rod in a sliding spiral transmission manner.

Preferably, the installation head is T-shaped, and a first open groove is formed in a head part of the installation head for connection to the first forcep handle, and a tail part of the installation head is connected to a spherical elastic groove; a spherical hinged joint of the rotating rod is rotatably connected in the spherical elastic groove; and a locking member is connected to a tail part of the installation head in a threaded manner, and the locking member acts on the spherical elastic groove to suppress relative movement between the spherical elastic groove and the rotating rod.

Preferably, an operating chamber is arranged inside the clamping head; an end face, backing away from the installation head, of the clamping head is provided with two inwardly recessed communicating grooves; the communicating groove is communicated with the operating chamber; the power component includes a fixed block, electric push rods, and a rotating node rod; the fixed block is installed inside the operating chamber; the two electric push rods are installed on the fixed block; the two clamping rods extend into the communicating grooves in one-to-one correspondence and are hinged to end parts of moving rods of the electric push rods in one-to-one correspondence; a rod body of the clamping rod is rotatably connected to the rotating node rod; and the rotating node rod is installed on the clamping head and spans the communicating groove.

Preferably, a cross section of the limiting clamp is U-shaped, and an inner wall of the limiting clamp is provided with an elastic clamping block; the clamping head is caught in the limiting clamp through the elastic clamping block; and outer sides of the first forcep handle and the second forcep handle are provided with antislip sleeves.

Preferably, a first installation groove is arranged inside the clamping head; a storage battery is arranged inside the first installation groove; and the storage battery is electrically connected to the power component.

Preferably, a camera is further installed on an end part, backing away from the installation head, of the clamping head; the storage battery is electrically connected to the camera; a second installation groove is arranged inside the clamping head, and an integrated circuit board is arranged inside the second installation groove; and the first forcep handle is provided with a control switch for controlling start and stop of the integrated circuit board.

Preferably, the integrated circuit board includes a control module, an image receiving and processing module, an image transmission module, and a wireless signal receiving module;

the wireless signal receiving module is configured to receive an external information instruction;

the control module is configured to process the information instruction received by the wireless signal receiving module and issue an instruction to the power component, or issue instructions to the image receiving and processing module and the image transmission module;

the image receiving and processing module is connected to the camera and configured to receive and denoise a picture captured by the camera; and the image transmission module is configured to transmit denoised image information to an external display device.

Preferably, the integrated circuit board includes a control module and a wireless signal receiving module;

the wireless signal receiving module is configured to receive an external information instruction;

the control module is configured to process the information instruction received by the wireless signal receiving module and issue an instruction to the power component; and a transmission line of the camera penetrates through the clamping head and extends from an end part, close to the installation head, of the clamping head for connection to an external display device.

Preferably, an end part, backing away from the camera, of the clamping rod is bent towards a position between the two clamping rods so as to form a space that can accommodate the camera between the two clamping rods.

Compared with the prior art, the present disclosure has the beneficial effects as follows.

(1) The first forcep handle can swing relative to the second forcep handle, and is clamped at different positions on the clamping head through the limiting clamp, such that opening and closing angles of the first forcep handle and the second forcep handle can be controlled. The two clamping rods approach to or move away from each other by the power component, thereby clamping the suture line or a suture needle and completing knotting. This can avoid manually holding the first forcep handle and the second forcep handle simultaneously for a long time. At the same time, the swing angle of the clamping head can be changed according to a required angle under the action of the limiting clamp, further improving the use convenience for the operator.

(2) By arranging the spherical elastic groove and the locking member, the swing angle of the clamping head can be roughly adjusted. By arranging the adjusting nut and the threaded rod, the swing angle of the clamping head can be finely adjusted so as to ensure the accuracy and stability of the swing angle of the clamping head.

(3) The camera is arranged between the two clamping rods, and can transmit a picture of a wound to the external display device, such that an external operator can have a clear and intuitive understanding of the wound situation through the external display device, thereby assisting in suturing and knotting. It is very suitable for minimally invasive surgery and improves the operation quality and use efficiency compared to a traditional knotter.

Figure 1:
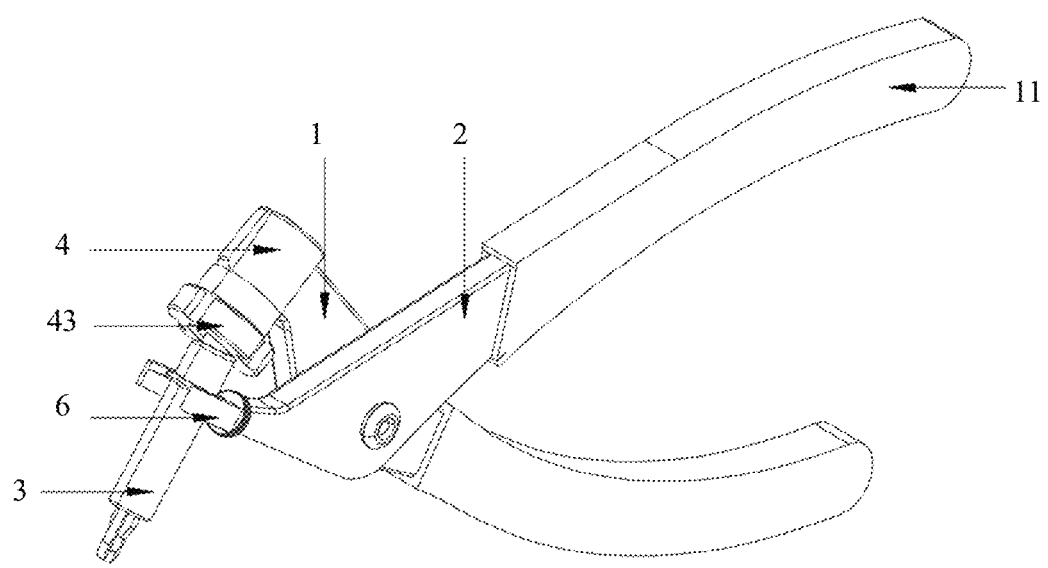
FIG. 1 is an isometric side view from a first perspective of a minimally invasive knotter of the present disclosure.

Reference numerals in the drawings: 1, first forcep handle, 11, antislip sleeve, 2, second forcep handle, 21, accommodating channel, 3, clamping head, 31, clamping rod, 32, operating chamber, 33, communicating groove, 34, first installation groove, 35, second installation groove, 4, installation head, 41, first open groove, 42, spherical elastic groove, 43, locking member, 5, rotating rod, 6, limiting clamp, 7, moving component, 71, threaded rod, 711, keyway, 72, adjusting nut, 721, connecting cylinder, 73, flat key, 8, power component, 81, fixed block, 82, electric push rod, 83, rotating node rod, 9, storage battery, 91, camera, 92, integrated circuit board, 93, control switch, 100, wireless signal receiving module, 200, control module, 300, image receiving and processing module, and 400, image transmission module.

DETAILED DESCRIPTION

The present disclosure will be described in detail in combination with the accompanying drawings.

It should be noted that the terms used in the present disclosure, such as "up", "down", "left", "right", "front", "back", etc., are only for the sake of clarity in description and are not intended to limit the scope of the present disclosure that can be implemented. Changes or adjustments in their relative relationships, without substantial changes in technical content, should also be considered as the scope of the present disclosure that can be implemented.

Figure 2:
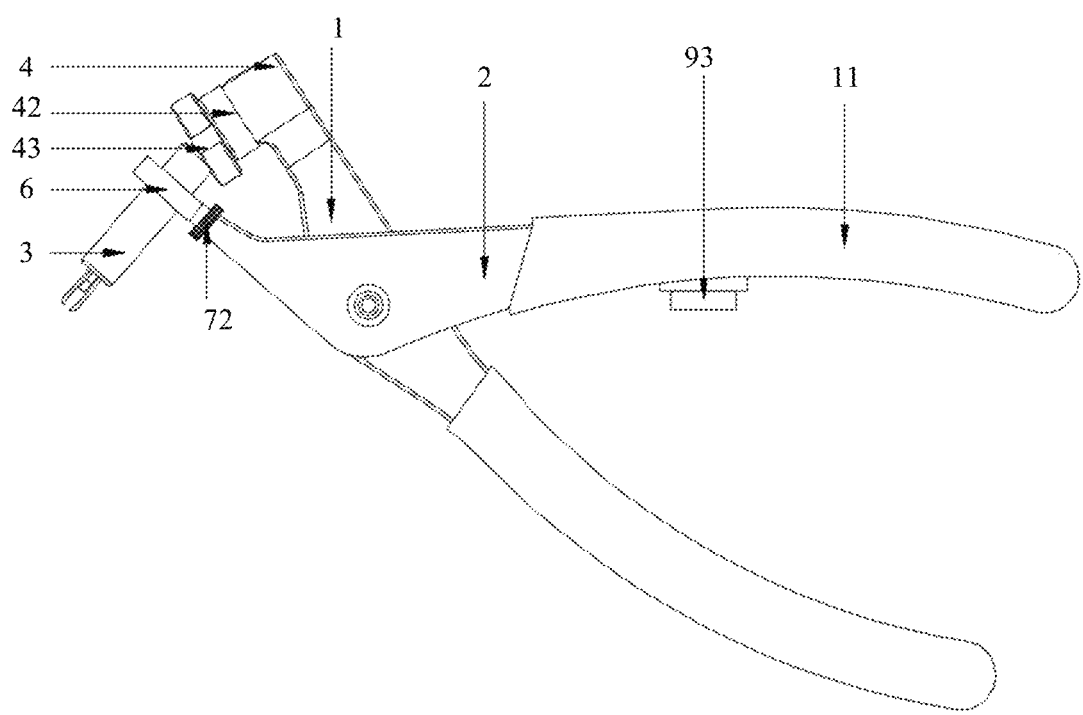
FIG. 2 is a front view of the minimally invasive knotter of the present disclosure.
Figure 3:
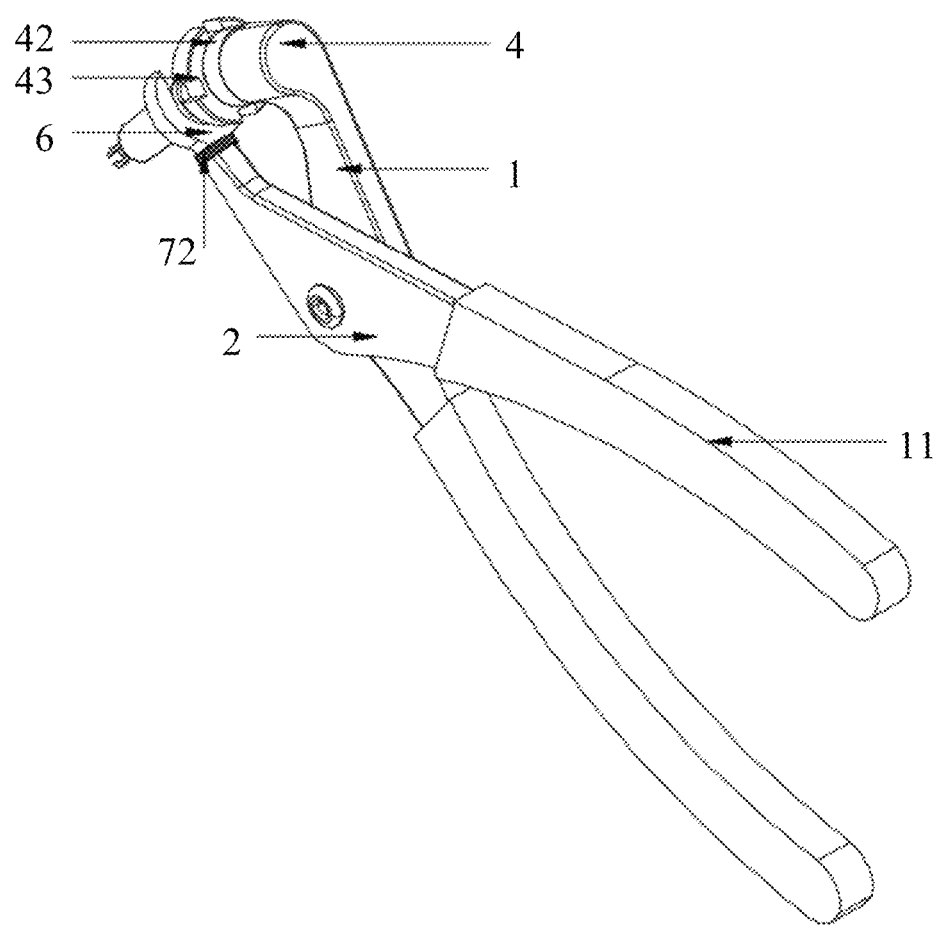
FIG. 3 is an isometric side view from a second perspective of the minimally invasive knotter of the present disclosure.

As shown in FIG. 1 to FIG. 3, a minimally invasive knotter includes a first forcep handle 1, a second forcep handle 2, and a clamping head 3. Middle parts of the first forcep handle 1 and the second forcep handle 2 intersect and are connected in a hinged manner. That is, the hinged first forcep handle 1 and second forcep handle 2 are X-shaped.

The first forcep handle 1 is provided with an installation head 4, and a rotating rod 5 is spherically hinged to the installation head 4. The clamping head 3 is connected to the rotating rod 5. The installation head 4 and the first forcep handle 1 may be welded into a whole or integrally molded, and the second forcep handle 2 is provided with a limiting clamp 6 and a moving component 7. One side of the limiting clamp 6 is provided with an opening capable of catching the clamping head 3. That is, the clamping head 3 and the rotating rod 5 are connected in a threaded manner or other detachable manners. Of course, they can also be connected by welding or in other non-detachable manners. The rotating rod 5 can rotate along the installation head 4 in a universal manner. The limiting clamp 6 is connected to the second forcep handle 2 through a moving component 7 so as to limit the clamping head 3 at a set angle.

Further, in order to ensure the clamping effect of the limiting clamp 6 on the clamping head 3, a cross section of the limiting clamp 6 is U-shaped, and an inner wall of the limiting clamp 6 is provided with an elastic clamping block. The clamping head 3 is caught in the limiting clamp 6 by the elastic clamping block. That is, when the clamping head 3 is clamped in the elastic clamping block, the elastic clamping block tightly surrounds an outer side of the clamping head 3, and the elastic clamping block itself has a certain friction force, thereby avoiding the clamping head 3 from disengaging from the elastic clamping block. The U-shaped limiting clamp 6 can also make the clamping head 3 disengage from the rotating rod 5 and the limiting clamp 6 when maintenance or cleaning is needed, thereby improving the practicality.

Further, outer sides of the first forcep handle 1 and the second forcep handle 2 are both provided with antislip sleeves 11, and the antislip sleeve 11 can improve comfort of an operator.

Figure 4:
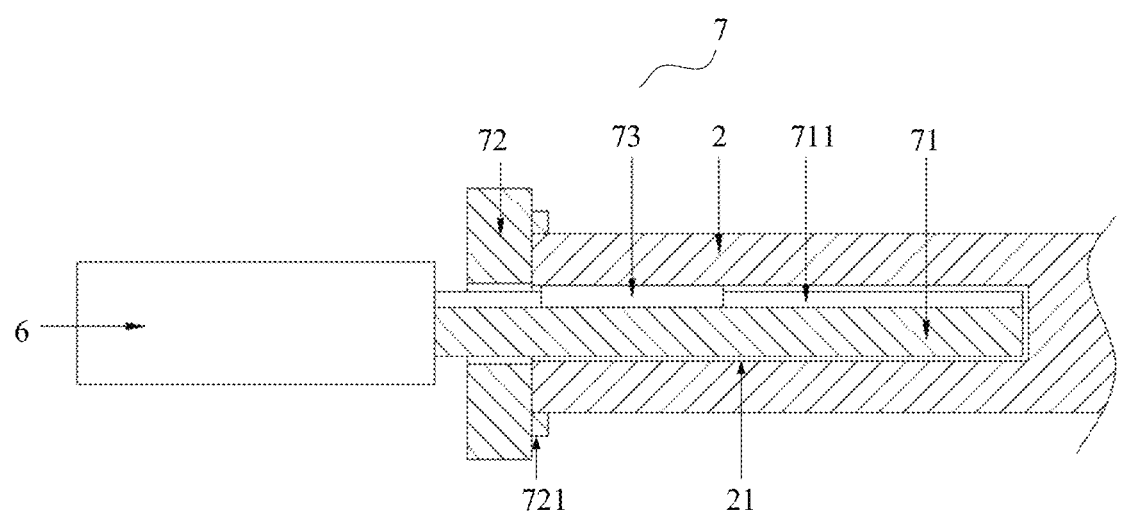
FIG. 4 is a schematic view of a connection state between a limiting clamp and a second forcep handle of the minimally invasive knotter of the present disclosure.

Specifically, as shown in FIG. 4, the moving component 7 includes a threaded rod 71, an adjusting nut 72, and a flat key 73. The second forcep handle 2 is provided with an accommodating channel 21 inwardly recessed from an end face. One end of the threaded rod 71 extends into the accommodating channel 21, and the other end is connected to the limiting clamp 6. The end, extending into the accommodating channel 21, of the threaded rod 71 is provided with a keyway 711, and the keyway 711 extends in an axial direction of the threaded rod 71. The flat key 73 is installed on a channel wall of the accommodating channel 21 and is slidably connected to the keyway 711. That is, under the action of the flat key 73 and the keyway 711, the threaded rod 71 can move back and forth in an axial direction of the threaded rod 71 relative to the accommodating channel 21. An end face of the adjusting nut 72 is provided with a connecting cylinder 721 extending in an axial direction thereof. The connecting cylinder 721 is rotatably connected to the second forcep handle 2. A threaded hole of the adjusting nut is connected to the threaded rod 71 in a sliding spiral transmission manner. By rotating the adjusting nut 72, the threaded rod 71 can move in a direction for screwing into or out of the accommodating channel 21, thereby changing a position of the limiting clamp 6 and a swing angle of the clamping head 3 relative to the installation head 4.

Figure 5:
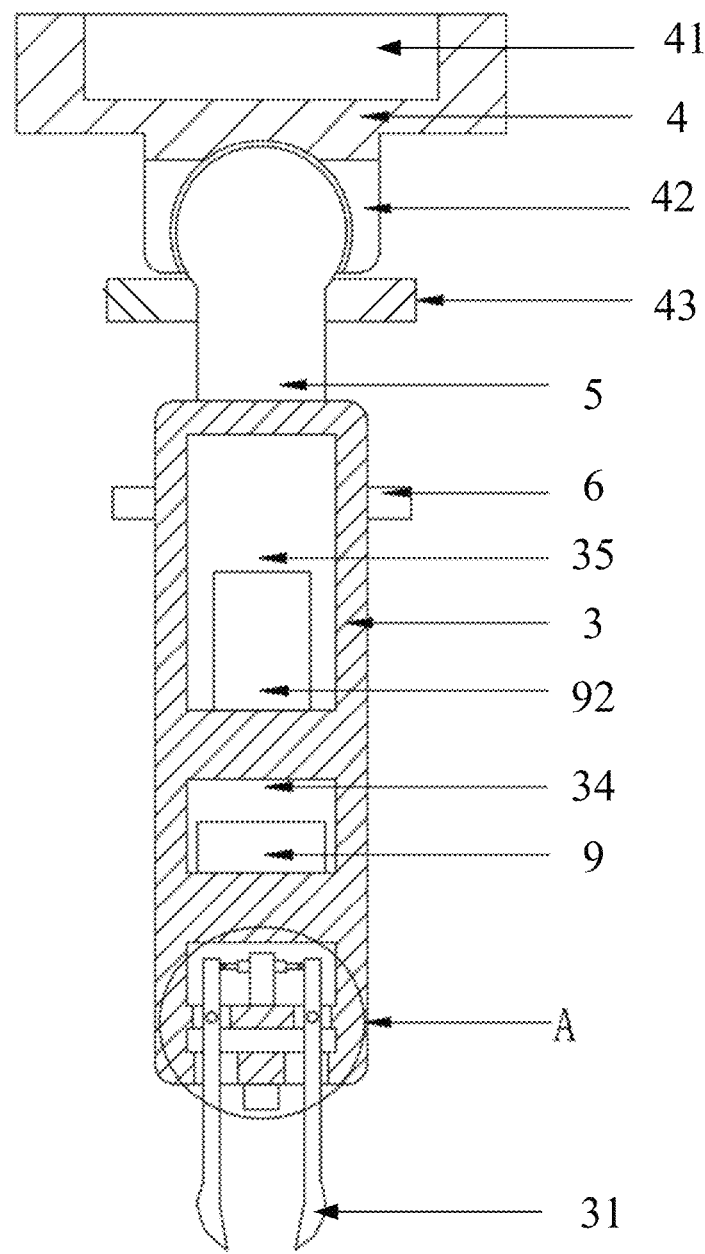
FIG. 5 is a schematic view of an internal structure of a clamping head of the minimally invasive knotter of the present disclosure.
Figure 6:
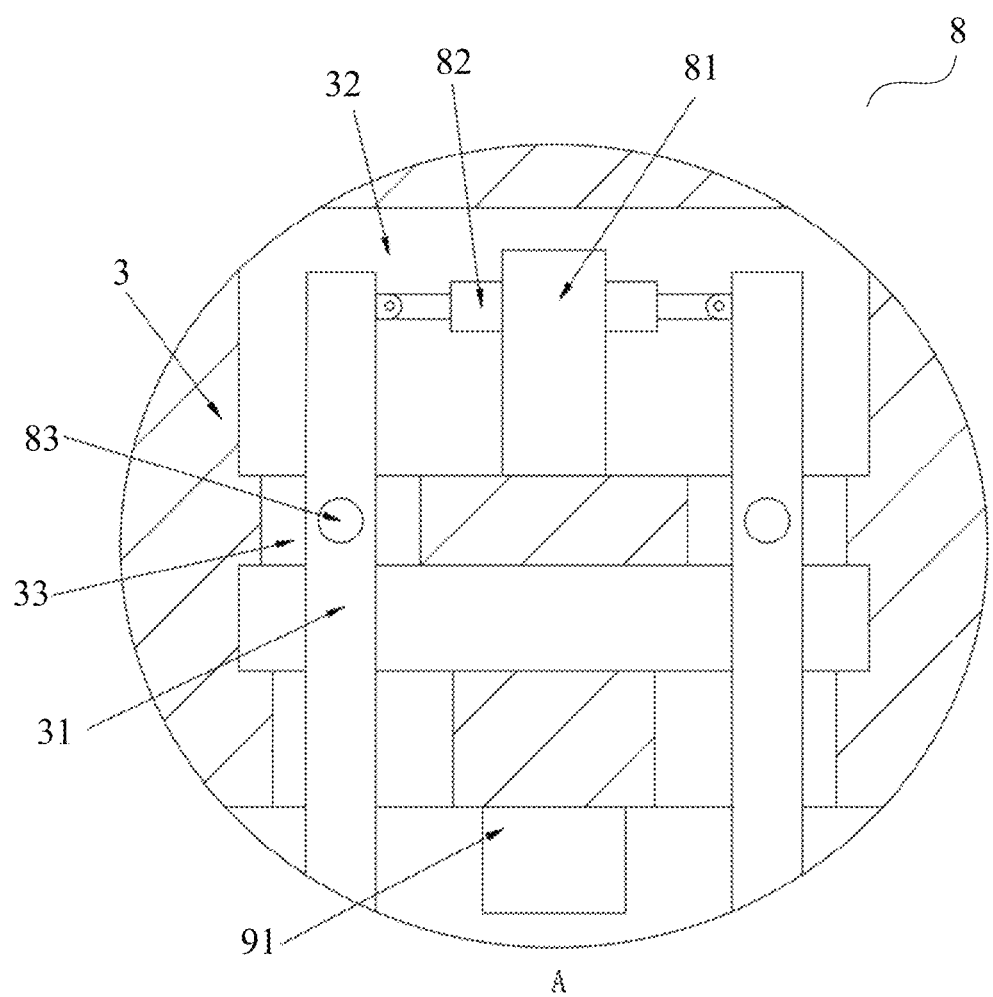
FIG. 6 is an enlarged structural schematic view of part A in FIG. 5 of the present disclosure.

Specifically, as shown in FIG. 5 and FIG. 6, an end part, backing away from the rotating rod 5, of the clamping head 3 is provided with two clamping rods 31. Under the action of a power component 8, the two clamping rods 31 can approach to or back away from each other to achieve clamping and releasing of a suture line. The two clamping rods 31 can be opened and closed by the power component 8, which can avoid the need for manually holding the first forcep handle 1 and the second forcep handle 2 at the same time for a long time. The swing angle of the clamping head 3 can be changed as needed, and the clamping head can be accurately limited at the set angle for use, further improving the use convenience of for an operator.

Specifically, an operating chamber 32 is arranged inside the clamping head 3. An end face, backing away from the installation head 4, of the clamping head 3 is provided with two inwardly recessed communicating grooves 33. The communicating groove 33 is communicated with the operating chamber 32. The power component 8 includes a fixed block 81, electric push rods 82, and a rotating node rod 83. The fixed block 81 is installed inside the operating chamber 32. The two electric push rods 82 are installed on the fixed block 81. The two clamping rods 31 extend into the communicating grooves 33 in one-to-one correspondence and are hinged to end parts of moving rods of the electric push rods 82 in one-to-one correspondence. A rod body of the clamping rod 31 is rotatably connected to the rotating node rod 83. The rotating node rod 83 is installed on the clamping head 3 and spans the communicating groove 33. Under the joint action of the two electric push rods 82, the two clamping rods 31 approach to or back away from each other. Of course, the two electric push rods 82 may also be two ball screws, or ball screws with different rotating directions at both ends. When the clamping rod 31 is driven by the ball screw, there is no need to arrange the rotating node rod 83, but a sliding guide rod may be arranged as needed.

In some other embodiments, the installation head 4 is T-shaped, and a first open groove 41 is formed in a head part of the installation head 4 for connection to the first forcep handle 1 in a threaded manner or in a fastened manner by other connecting members, and a tail part of the installation head 4 is connected to a spherical elastic groove 42. A structure of the elastic groove may be a semi-spherical structure made of a rubber material, which can be squeezed. Of course, it may also be a semi-spherical structure defined by multiple elastic sheets with a certain gap. A spherical hinged joint of the rotating rod 5 is rotatably connected in the spherical elastic groove 42. A locking member 43 is connected to a tail part of the installation head 4 in a threaded manner, and the locking member 43 acts on the spherical elastic groove 42 to suppress relative movement between the spherical elastic groove 42 and the rotating rod 5. That is, when the rotating rod 5 rotates relative to the spherical elastic groove 42 to a set angle, the locking member 43 wraps an outer side of the elastic groove, thereby avoiding relative movement between the spherical elastic groove 42 and the rotating rod 5. The locking member 43 may be a threaded cylinder or a fastening nut. That is, by arranging the locking member 43, the elastic groove, and the rotating rod 5, the swing angle of the clamping head 3 can be greatly controlled. By arranging the spherical elastic groove 42 and the locking member 43, the swing angle of the clamping head 3 can be roughly adjusted; and by arranging the adjusting nut 72 and the threaded rod 71, the swing angle of the clamping head 3 can be finely adjusted to ensure the accuracy and stability of the swing angle.

In some other embodiments, a first installation groove 34 is arranged inside the clamping head 3. A storage battery 9 is arranged inside the first installation groove 34. The storage battery 9 is electrically connected to the power component 8. A structure of the storage battery 9 can refer to the prior art. A power supply of the power component 8 may also be connected to a power cord through an external power source.

Figure 7:
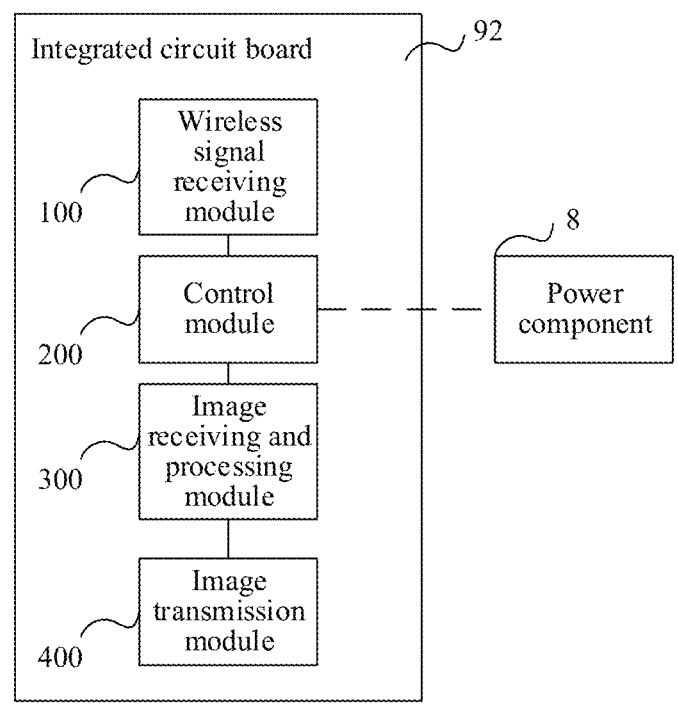
FIG. 7 is a module block view of an integrated circuit board of the minimally invasive knotter of the present disclosure.

In some other embodiments, a camera 91 is further installed on an end part, backing away from the installation head 4, of the clamping head 3. Specifically, an end part, backing away from the camera 91, of the clamping rod 31 is bent towards a position between the two clamping rods 31 so as to form a space that can accommodate the camera 91 between the two clamping rods 31. The storage battery 9 is electrically connected to the camera 91. A second installation groove 35 is arranged inside the clamping head 3, and an integrated circuit board 92 is arranged inside the second installation groove 35. The first forcep handle 1 is provided with a control switch 93 for controlling start and stop of the integrated circuit board 92. In one embodiment, as shown in FIG. 7, the integrated circuit board 92 includes a control module 200, an image receiving and processing module 300, an image transmission module 400, and a wireless signal receiving module 100.

Specifically, the wireless signal receiving module 100 is configured to receive an eternal information instruction. The control module 200 is configured to process the information instruction received by the wireless signal receiving module 100 and issue an instruction to the power component 8, and issue instructions to the image receiving and processing module 300 and the image transmission module 400.

The image receiving and processing module 300 is connected to the camera 91 and configured to receive and denoise a picture captured by the camera 91. Specifically, partial codes for image denoising is:

import cv2
Read an image
image=cv2.imread ('input_image.jpg')
Convert the image to a grayscale image
gray_img=cv2.cvtColor (image, cv2.COLOR_BGR2GRAY)
Use a mean filter for denoising
denoised_img=cv2.blur (gray_img, (3, 3)) #Adjust the size of the filter to control the degree of denoising
Display an original image and a denoised image
cv2.imshow ('Original Image', gray_img)
cv2.imshow ('Denoised Image', denoised_img)
cv2.waitKey(0)
cv2.destroy AllWindows ( )

The image transmission module 400 is configured to transmit the image information denoised by the image receiving and processing module 300 to an external display device for achieving remote image browsing, sharing, storage, or processing.

Figure 8:
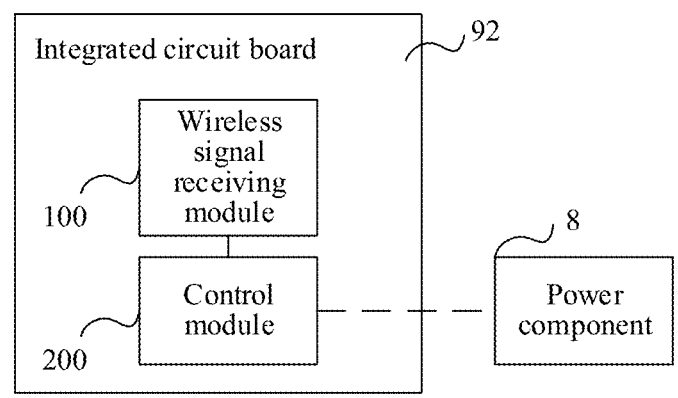
FIG. 8 is a module block view of another integrated circuit board of the minimally invasive knotter of the present disclosure.

In another embodiment, as shown in FIG. 8, the integrated circuit board 92 includes a control module 200 and a wireless signal receiving module 100. The wireless signal receiving module 100 is configured to receive an external information instruction. The control module 200 is configured to process the information instruction received by the wireless signal receiving module 100 and issue an instruction to the power component 8. A transmission line of the camera 91 penetrates through the clamping head 3 and extends from an end part, close to the installation head 4, of the clamping head 3 for connection to the external display device. That is, the picture captured by the camera 91 is directly transmitted to an external device through the transmission line, and the picture of the camera 91 is processed and displayed by the external device.

According to a working mode of the present disclosure, in use, the clamping head 3 is connected to the rotating rod 5, and the rotating rod 5 is rotated to achieve relative rotation between the rotating rod 5 and the spherical elastic groove 42, such that the clamping head 3 swings at the set angle. The opening and closing angles of the first forcep handle 1 and the second forcep handle 2 are adjusted, the adjusting nut 72 is rotated to make the threaded rod 71 translate in an axial direction thereof, and the clamping head 3 is clamped into the limiting clamp 6, thereby completing angle adjustment of the clamping head 3 and adjustment of length of the clamping head 3 extending out of the limiting clamp 4. The electric push rods 82 are used to drive the two clamping rods 31 to rotate, so that the two clamping rods 31 cooperatively rotate to achieve clamping of the suture line, thereby completing knotting. In addition, before and after knotting, the camera 91 may be used to capture an image and transmit the image to the external display device, so that an external operator can understand the condition of the wound inside the body through the external display device and perform suturing and knotting.

Various embodiments in this specification are described in a progressive manner, with each embodiment emphasizing its differences from other embodiments. The same or similar parts between the various embodiments can be referred to each other.

Those skilled in the art may clearly learn that the technology in the embodiments of the present disclosure may be implemented by relying on software and an essential common hardware platform.

The above are only preferred embodiments of the present disclosure, and the scope of protection of the present disclosure is not limited to the above embodiments. Any technical solution belonging to the concept of the present disclosure is within the scope of protection of the present disclosure. It should be noted that, for a person of ordinary skill in the art, several improvements and refinements without departing from the principle of the present disclosure shall fall within the protection scope of the present disclosure.

What is claimed is:

1. A minimally invasive knotter, comprising a first forcep handle (1), a second forcep handle (2), and a clamping head (3); middle parts of the first forcep handle (1) and the second forcep handle (2) intersect and are connected in a hinged manner, the first forcep handle (1) is provided with an installation head (4), and a rotating rod (5) is spherically hinged to the installation head (4); the clamping head (3) is connected to the rotating rod (5);

the second forcep handle (2) is provided with a limiting clamp (6) and a moving component (7); one side of the limiting clamp (6) is provided with an opening capable of catching the clamping head (3); the limiting clamp (6) is connected to the second forcep handle (2) through the moving component (7) so as to limit the clamping head (3) to work at a set angle; and an end part, backing away from the rotating rod (5), of the clamping head (3) is provided with two clamping rods (31), and under the action of a power component (8), the two clamping rods (31) are able to approach to or back away from each other to achieve clamping and releasing of a suture line.

2. The minimally invasive knotter according to claim 1, wherein the moving component (7) comprises a threaded rod (71), an adjusting nut (72), and a flat key (73); the second forcep handle (2) is provided with an accommodating channel (21) inwardly recessed from an end face; one end of the threaded rod (71) extends into the accommodating channel (21) and the other end is connected to the limiting clamp (6); the end, extending into the accommodating channel (21), of the threaded rod (71) is provided with a keyway (711) extending in an axial direction of the threaded rod (71); the flat key (73) is installed on a channel wall of the accommodating channel (21) and is slidably connected to the keyway (711); an end face of the adjusting nut (72) is provided with a connecting cylinder (721) extending in an axial direction thereof; the connecting cylinder (721) is rotatably connected to the second forcep handle (2); and a threaded hole of the adjusting nut (72) is connected to the threaded rod (71) in a sliding spiral transmission manner.

3. The minimally invasive knotter according to claim 1, wherein the installation head (4) is T-shaped, and a first open groove (41) is formed in a head part of the installation head (4) for connection to the first forcep handle (1), and a tail part of the installation head (4) is connected to a spherical elastic groove (42); a spherical hinged joint of the rotating rod (5) is rotatably connected in the spherical elastic groove (42); and a locking member (43) is connected to the tail part of the installation head (4) in a threaded manner, and the locking member (43) acts on the spherical elastic groove (42) to suppress relative movement between the spherical elastic groove (42) and the rotating rod (5).

4. The minimally invasive knotter according to claim 1, wherein an operating chamber (32) is arranged inside the clamping head (3); an end face, backing away from the installation head (4), of the clamping head (3) is provided with two inwardly recessed communicating grooves (33); the communicating groove (33) is communicated with the operating chamber (32); the power component (8) comprises a fixed block (81), an electric push rods (82), and a rotating node rod (83); the fixed block (81) is installed inside the operating chamber (32); the two electric push rods (82) are installed on the fixed block (81); the two clamping rods (31) extend into the communicating grooves (33) in one-to-one correspondence and are hinged to end parts of moving rods of the electric push rods (82) in one-to-one correspondence; a rod body of the clamping rod (31) is rotatably connected to the rotating node rod (83); and the rotating node rod (83) is installed on the clamping head (3) and spans the communicating groove (33).

5. The minimally invasive knotter according to claim 1, wherein a cross section of the limiting clamp (6) is U-shaped, and an inner wall of the limiting clamp (6) is provided with an elastic clamping block; the clamping head (3) is caught in the limiting clamp (6) through the elastic clamping block; and outer sides of the first forcep handle (1) and the second forcep handle (2) are provided with antislip sleeves (11).

6. The minimally invasive knotter according to claim 1, wherein a first installation groove (34) is arranged inside the clamping head (3); a storage battery (9) is arranged inside the first installation groove (34); and the storage battery (9) is electrically connected to the power component (8).

7. The minimally invasive knotter according to claim 6, wherein a camera (91) is further installed on an end part, backing away from the installation head (4), of the clamping head (3); the storage battery (9) is electrically connected to the camera (91); a second installation groove (35) is arranged inside the clamping head (3), and an integrated circuit board (92) is arranged inside the second installation groove (35); and the first forcep handle (1) is provided with a control switch (93) for controlling start and stop of the integrated circuit board (92).

8. The minimally invasive knotter according to claim 7, wherein the integrated circuit board (92) comprises a control module (200), an image receiving and processing module (300), an image transmission module (400), and a wireless signal receiving module (100);
the wireless signal receiving module (100) is configured to receive an external information instruction;
the control module (200) is configured to process the information instruction received by the wireless signal receiving module (100) and issue an instruction to the power component (8), and issue instructions to the image receiving and processing module (300) and the image transmission module (400);
the image receiving and processing module (300) is connected to the camera (91) and configured to receive and denoise a picture captured by the camera (91); and
the image transmission module (400) is configured to transmit image information denoised by the image receiving and processing module (300) to an external display device.

9. The minimally invasive knotter according to claim 7, wherein the integrated circuit board (92) comprises a control module (200) and a wireless signal receiving module (100);
the wireless signal receiving module (100) is configured to receive an external information instruction;
the control module (200) is configured to process the information instruction received by the wireless signal receiving module (100) and issue an instruction to the power component (8); and
a transmission line of the camera (91) penetrates through the clamping head (3) and extends from an end part, close to the installation head (4), of the clamping head (3) for connection to an external display device.

10. The minimally invasive knotter according to claim 7, wherein an end part, backing away from the camera (91), of the clamping rod (31) is bent towards a position between the two clamping rods (31) so as to form a space that can accommodate the camera (91) between the two clamping rods (31).

\* \* \* \* \*